United States Patent
Liu et al.

(10) Patent No.: US 9,593,151 B2
(45) Date of Patent: Mar. 14, 2017

(54) USE OF FUSION PROTEIN

(71) Applicant: East China University of Science & Technology, Shanghai (CN)

(72) Inventors: Changsheng Liu, Shanghai (CN); Wanli Xing, Shanghai (CN); Jing Wang, Shanghai (CN); Jiangchao Qian, Shanghai (CN); Jing Liang, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 14/653,276

(22) PCT Filed: Dec. 5, 2013

(86) PCT No.: PCT/CN2013/088671
§ 371 (c)(1),
(2) Date: Jun. 18, 2015

(87) PCT Pub. No.: WO2014/094546
PCT Pub. Date: Jun. 26, 2014

(65) Prior Publication Data
US 2015/0337025 A1    Nov. 26, 2015

(30) Foreign Application Priority Data
Dec. 18, 2012 (CN) .......................... 2012 1 0553208

(51) Int. Cl.
| | |
|---|---|
| *A61K 31/18* | (2006.01) |
| *A61K 31/664* | (2006.01) |
| *C07K 14/51* | (2006.01) |
| *A61K 38/18* | (2006.01) |
| *A61K 38/19* | (2006.01) |
| *A61K 9/00* | (2006.01) |

(52) U.S. Cl.
CPC ............ *C07K 14/51* (2013.01); *A61K 31/664* (2013.01); *A61K 38/1875* (2013.01); *A61K 38/193* (2013.01); *A61K 9/0019* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 5,879,673 A | * | 3/1999 | Thomas | ............... C07K 14/524 424/192.1 |
| 7,423,029 B1 | * | 9/2008 | Kiss | ........................ A61K 31/20 514/183 |
| 7,947,821 B2 | | 5/2011 | Liu et al. | |
| 2006/0128800 A1 | * | 6/2006 | Penney | ................... A61K 31/20 514/517 |
| 2006/0233748 A1 | * | 10/2006 | Merzouk | ............ C07K 14/5421 424/85.2 |

FOREIGN PATENT DOCUMENTS

| | | |
|---|---|---|
| CN | 1951964 A | 4/2007 |
| CN | 101787369 | 7/2010 |
| CN | 102973922 A | 3/2013 |

\* cited by examiner

*Primary Examiner* — David Romeo
(74) *Attorney, Agent, or Firm* — Adam Bell; Matthew Kaser

(57) ABSTRACT

Disclosed is the use of a fusion protein in drugs for stimulating differentiation of bone marrow mesenchymal stem cells to hematopoietic stem/progenitor cells, or drugs for proliferation of granulocyte hematopoietic progenitor cells. The fusion protein has a sequence as shown in SEQ ID NO: 2 or SEQ ID NO: 4. The drugs can be used for the prevention and/or treatment of (i) hematopoietic dysfunction caused by chemotherapy, (ii) hematopoietic dysfunction caused by radiotherapy, or (iii) leukopenia.

12 Claims, 3 Drawing Sheets

USE OF FUSION PROTEIN

FIELD OF THE INVENTION

The invention relates to the application of a fusion protein. Specifically, the invention relates to the use of a fusion protein in promoting the proliferation of granulocytic hematopoietic progenitor cell.

BACKGROUND OF THE INVENTION

Blood has many physiological functions such as, transporting materials, maintaining the excitability of the tissue, regulation and defense functions. Therefore, blood is one of the basic materials which constitutes human body and sustains human activities. It could cause serious consequences once the composition of blood changes abnormally. Many factors, such as, chemical, physics, and biological reasons, etc., can be direct or indirect reasons which cause blood diseases. Thereinto many of the factors are generated along with the development of modern industry, thereby resulting the rising incidence of blood diseases in recent years.

Bone marrow inhibitory anemia is a common type of anemia caused by chemical, physical, biological factors and unexplained reasons, which expresses as the decrease of bone marrow hematopoietic tissue and the failure of hematopoietic function. Bone marrow suppression can induce damages of bone marrow microenvironments, hematopoietic stem cells, hematopoietic growth factors and the like. What's more, the granulocyte, megakaryocyte cell system can also be restrained, and the lack of granulocytes will cause serious infection.

At present, radiotherapy and chemotherapy are still the most commonly methods used in tumors treatment. But most patients will experience adverse reactions such as nausea and emesis after treatment. Bone marrow inhibition which is the most common and serious adverse reaction can not only decrease hematopoietic function, reduce immunity, which will lead to the failure of normal-dose chemotherapy and affect the continuity of chemotherapy, but also reduce white blood cells and platelets, which will increase the incidence of infection and haemorrhage, even cause death. Promoting recovery of hematopoietic function of the patient rapidly is the key point to raise the cure rate of the cancer, reduce the incidence of infection and improve the quality of life of the patient.

Currently, colony stimulating factors, such as granulocyte colony stimulating factor (G-CSF), granulocyte macrophage colony stimulating factor (GM-CSF) and the like, are widely used to promote the recovery of hematopoietic function clinically. Such colony stimulating factors directly stimulate the proliferation of granulocytic hematopoietic progenitor cell, which can expedite the recovery of white blood cells and neutrophils and obtain rapid curative effect. But CSF directly stimulate the proliferation of none self-renewal hematopoietic progenitor cells, which will result in the depletion of hematopoietic progenitor cells and compromise the long-term recovery of hematopoietic function, even lead to deficiency of bone marrow reserve. Furthermore, some tumor cells, such as leukemia cells, have the normal receptor of CSF, so medication may increase the proliferation of residual tumor cells in host, then raise the tumor recurrence rate. At the same time, due to the poor stability of CSF, a large number of immature white blood cells flood the peripheral blood and bone marrow, which lead to the white blood cell count changes dramatically. Patients have to take medication repeatedly to maintain the normal treatment course. Therefore, a novel drug which can promote the proliferation of hematopoietic progenitor cells and has no promotion to the proliferation of tumor cells should be developed clinically.

SUMMARY OF THE INVENTION

The object of this invention is to provide a use of a fusion protein which can promote the proliferation of granulocytic hematopoietic progenitor cell.

Another object of this invention is to provide a pharmaceutical composition used in promoting the proliferation of hematopoietic cells (predominantly the granulocytes).

The third object of the invention is to provide a method to promote the granulocytes proliferation in vitro.

In the first aspect, the invention provides a use of a fusion protein, wherein the sequences of the fusion protein is shown in SEQ ID NO: 2 or SEQ ID NO: 4, the fusion protein is used to prepare (i) a drug for stimulating the differentiation of bone marrow mesenchymal stem cells to hematopoietic stem/progenitor cells; or (ii) a drug for promoting the proliferation of granulocytic hematopoietic progenitor cells.

In a preferred embodiment, the drug is used to:

(1) prevent and/or treat the depressed hematopoietic function caused by chemotherapy;

(2) prevent and/or treat the depressed hematopoietic function caused by radiotherapy; or (3) prevent and/or treat leukopenia.

In a preferred embodiment, the drug is used before, during, and/or after radiotherapy or chemotherapy.

In the second aspect, the invention provides a use of a fusion protein, wherein the sequence of the fusion protein is shown in SEQ ID NO: 2 or SEQ ID NO: 4, the fusion protein is used to promote the proliferation of granulocytic hematopoietic progenitor cells.

In a preferred embodiment, the fusion protein is used to promote the proliferation of granulocytic hematopoietic progenitor cells in vitro.

In the third aspect, the invention provides a use of a fusion protein, wherein the sequence of the fusion protein is shown in SEQ ID NO: 2 or SEQ ID NO: 4, the fusion protein is used to prepare a drug for preventing and/or treating leukopenia.

In the fourth aspect, the invention provides a method for promoting the proliferation of granulocytic progenitor cells in vitro, comprising adding 100 ng/mL~5 µg/mL fusion protein to the culture medium of granulocytic progenitor cells, wherein the sequence of the fusion protein is shown in SEQ ID NO: 2 or SEQ ID NO: 4.

Wherein, the granulocytic progenitor cells are granulocytic hematopoietic progenitor cells.

In the fifth aspect, the invention provides a pharmaceutical composition comprising:

a fusion protein, wherein the sequence of the fusion protein is shown in SEQ ID NO: 2 or SEQ ID NO: 4; and pharmaceutically acceptable carrier or excipient.

The pharmaceutical composition of the present invention is non-toxic and has stable dosage form.

In a preferred embodiment, the pharmaceutical composition is used before, during, and/or after radiotherapy or chemotherapy.

In a preferred embodiment, the pharmaceutical composition comprises cyclophosphamide.

In the sixth aspect, the invention provides a use of the drug combination mentioned in the fifth aspect in preparing a drug for promoting the proliferation of granulocytic hematopoietic progenitor cells.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figure 1:
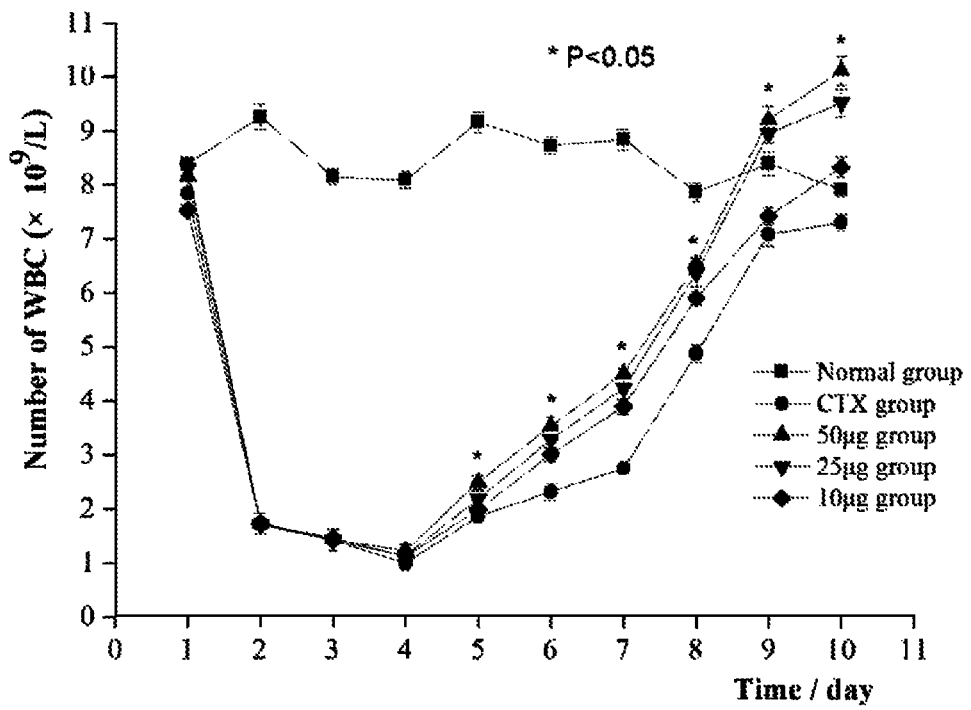
FIG. 1 shows the leukocyte (WBC) trends of mice in each group at different time.

After extensive and intensive research, the inventor of this application accidentally found that the fusion protein used in this invention can not only promote the proliferation of granulocytic hematopoietic progenitor cells, but also can effectively prevent and treat the depressed hematopoietic function caused by chemotherapy or radiotherapy and the decrease of white blood cells. On this basis, the invention is completed.

Fusion Protein

The amino acid sequence of the fusion protein used in the present invention is shown in SEQ ID NO: 2 or SEQ ID NO: 4. The molecular weight of single strand protein is about 13-15 kD. After renaturation, the active protein is dimer and the molecular weight is about 25-30 kD. The fusion protein used in this invention has good activity and stability, enhanced expression, promoted the correct fold when protein renaturation, and extended biologic half life and increased the effect in the body. In addition, the fusion protein is easy to renature and separate. It also has high activity and is suitable for industrialized fabrication and application.

Use of Fusion Protein

The fusion protein mentioned in this invention (the amino acid sequence of the fusion protein as shown in SEQ ID NO: 2 or SEQ ID NO: 4) can be used to prepare (i) a drug which can stimulate the differentiation of bone marrow mesenchymal stem cells to hematopoietic stem/progenitor cells; or (ii) a drug which can promote the proliferation of granulocytic hematopoietic progenitor cells.

The drug can be used to:

(1) prevent and/or treat the depressed hematopoietic function caused by chemotherapy;

(2) prevent and/or treat the depressed hematopoietic function caused by radiotherapy;

(3) prevent and/or treat leukopenia.

In a preferred embodiment, the drug is used to prevent and/or treat leukopenia.

The drug is used before, during, and/or after radiotherapy or chemotherapy.

The scientific study shows that the fusion protein of this invention can promote the recovery of depressed hematopoietic function caused by chemotherapy/radiotherapy.

The fusion protein has effective therapeutical effect for hematopoietic injury caused by chemotherapy. The promoting hematopoiesis effect of the fusion protein mainly relates to bone marrow stromal cells. The fusion protein can improve the hematopoietic microenvironment, thus it can affect the proliferation and differentiation of hematopoietic stem/progenitor cells. Determination of the number of bone marrow nucleated cells or bone marrow granulocyte colonies is the most direct evidence of the bone marrow hyperplasia. Furthermore, the detections of CD34 and CD45 cells are the most direct evidences reflecting the proliferation and differentiation of hematopoietic stem/progenitor cells.

The intraperitoneal injection of the fusion protein of the present invention can promote the recovery of the number of bone marrow nucleated cells and peripheral blood leukocyte in the mice treated with cyclophosphamide. Significant difference can be observed compared with the control group treated with cyclophosphamide, which indicates that the fusion protein mentioned in this invention mainly promotes granulocytic hematopoiesis. Thus, the fusion protein mentioned in this invention can be regarded as a kind of effective promoting hematopoietic factor and has clinical application prospects in promoting granulocyte hematopoiesis.

In addition, hematopoietic microenvironment is one of the prerequisites of normal hematopoiesis. The fusion protein used in the present invention improves the hematopoietic microenvironment via stimulating the proliferation of bone marrow mesenchymal stem cell and promotes the recovery of the spontaneous or induced inhibition of bone marrow or the damage of hematopoietic function. It also can stimulate the hematopoietic reconstruction after bone marrow transplantation.

This invention provides an effective drug for preventing/treating depressed hematopoietic function, leukopenia and so on.

Pharmaceutical Composition

The pharmaceutical composition comprises the fusion protein used in the present invention.

The pharmaceutical composition of the present invention can improve proliferation of hematopoietic stem/progenitor cells and promote the recovery of hematopoietic function. It can used to treat the depressed hematopoietic function caused by bone marrow damage resulted from chemotherapy, radiotherapy or spontaneous generation.

Compared with currently wide used recombinant human granulocyte colony stimulating factor (rhG-CSF) and recombinant human granulocyte macrophage colony stimulating factor (rhGM-CSF) clinically, the fusion protein used in the present invention has mild effect on promoting proliferation of blood cells and can accelerate the recovery process of peripheral blood cells. Thus the fusion protein used in the present invention has a wide prospect in clinical application. Moreover, the fusion protein is hard to cause immunogenicity.

The fusion protein or pharmaceutical composition of the present invention can be fabricated as a drug which meets the specific clinical method of administration according to the conventional methods well-known in the pharmaceutical field. For example, the appropriate carrier or diluent, such as water, saline solution or isotonic glucose solution, can be added into the fusion protein or pharmaceutical composition of the present invention to fabricate injection solution which can be administrated by any route except gastrointestinal delivery. Other excipients or carriers, such as starch, lactose, sucrose, glucose, glycerol, liposomes, gelatin, mannitol and the like can also be added.

The fusion protein or pharmaceutical composition of the present invention can be injected through conventional routes, such as intravenous injection, intraperitoneal injection, muscle injection and the like.

The characteristics mentioned above in this invention or embodiments can be combined arbitrarily. All the characteristics mentioned in this specification can be applied in any combination. The characteristics mentioned in this invention can be replaced by any alternative characteristics which offer the same, equal or similar purposes. Unless otherwise specified, the revealed characteristics are only general examples of the equal or similar characteristics.

The invention is further illustrated by the following examples. It is appreciated that these examples are only intended to illustrate the invention, but not to limit the scope of the invention. The experimental methods which do not contain specific experimental conditions in the following examples are performed under routine conditions, e.g., just like those described by Sambrook. et al., in Molecule Cloning: A Laboratory Manual, New York: Cold Spring Harbor Laboratory Press, 1989, or as instructed by the manufacturers. Unless otherwise specified, the percentage and number is calculated by weight.

Example 1

The Preparation of Fusion Protein

1. Construction of Recombinant Vectors

DNA sequence (SEQ ID NO: 1) was synthesized by gene synthesis method. Then, the gene was digested by enzyme and inserted into the conventional vector pBV220. The optimized rhBMP-2 expression plasmid was obtained, the inserted elements were confirmed by restriction enzyme digestion and sequencing and were consistent with the design.

2. Construction, Verification and Storage of Engineered Bacteria

Competent expression system was prepared by the conventional calcium chloride method by using molecular cloning technique. The competent *E. coli* (JM109) was transformed by the expression plasmid obtained in step 2. From the LB plate with appropriate antibiotics, several positive colonies were picked and cultured overnight in LB. Plasmid DNA was isolated and analyzed by restriction enzyme digestion and sequencing to confirm the presence of the correct expression vector. Once the correct clone was identified, the colony was purified and inoculated into flasks containing LB culture medium with glucose and antibiotics, cultured for 15 hrs under the condition of 180 rpm and 30° C. in air bath shaker. Sterile glycerol was mixed with the culture to make a glycerol stock of the recombinant cell with the final glycerol concentration of 15%. The glycerol stock was transferred to a cryovial and stored at −80° C. freezer.

3. Culture of Engineered Bacteria

From the glycerol stock of the engineered bacteria, the original colony was streaked out for single colonies on an LB plate containing appropriate antibiotics. A single colony was isolated and inoculated into LB culture medium containing 10 g/L tryptone, 5 g/L yeast extract, 5 g/L NaCl and 100 μg/mL penbritin. After 8 hrs' culture under the condition of 180 rpm and 30° C. in air bath shaker, the culture was inoculated into LB culture medium with volume ratio of 1:10 and cultured for 4 hrs under the condition of 180 rpm, 30° C., and pH 7.0±0.2. After that, temperature was raised to 42° C. and the mixture was cultured for another 6 hrs. At the end of culture, the medium was centrifuged (7500 rpm) at 4±2° C., and bacteria were collected and disrupted. The polyacrylamide gel electrophoresis (PAGE) was run to analyze the cell lysis. Compared to recombinant bacteria before induction and blank bacteria without plasmid, a clear band corresponding to molecular weight of 15 KD was observed, which indicated that the objective protein was obtained.

4. Extraction and Wash of Inclusion Bodies

The bacteria collected in step 3 was mixed with TE solution at the ratio of 1 g:10 ml, and then lysozyme was added at the ratio of 1 g:1 mg. The bacteria were broken by cell disruption technique and centrifuged at 10000 rpm. After that, the precipitate was collected and mixed with 1 M aqueous urea solution at the ratio of 1 g:20 ml (precipitate:washing buffer) to wash. After 2 hrs stirring, the cell lysis was collected by centrifugation at 4±2° C., washed again with 0.5% of aqueous triton solution. Then, the cell lysis was washed with 10 mM Tris (pH 7.5) solution at the ratio of 1 g:20 ml (precipitate:Tris), and the precipitate was collected to obtain inclusion bodies.

5. Lysis and Renaturation of Inclusion Bodies

Lysis solution comprising 6 M Gu-HCl, 20 mM PBS and 10 mM DTT was added at the ratio of 1 g:10 mL (inclusion bodies:lysis solution), stirred to dissolve inclusion body precipitate for 8 hrs at 4±2° C., and centrifuged for 30 mM at 10000 rpm and 4±2° C. The supernatant was collected, diluted to 0.1 mg/mL of protein level, then mixed with refolding solution to renature for 10d. The refolding solution contained 20 mM $Na_2HPO_4.12H_2O$, 1.5 mM $NaH_2PO_4.2H_2O$, 140 mM NaCl, 5 mM EDTA and 1 mM glutathione.

6. Purification of Protein

Bioactive dimer of rhBMP-2 was recovered from refolding solution by conventional purification processes, such as anion-exchange chromatography, cation-exchange chromatography, and molecular-exclusion chromatography. And then the obtained fusion rhBMP-2 was lyophilized at −30~7° C., the amino acid sequence is shown in SEQ ID NO: 2.

The results determined by non-reducing SDS-PAGE indicated that the protein purity was above 95% and the molecular weight was about 30 KD. HLPC analysis also showed that the purity was above 95%. Also, the sequences of N-terminus and C-terminus were the same as those deduced from the nucleotide sequences.

The average yield of rhBMP-2 was 7.02 mg/L.

Example 2

The Promoting Hematopoiesis of Fusion Protein in the Model of Chemotherapy 2.1 The purpose of this example was to observe the therapeutical effect of fusion protein for leukopenia caused by chemotherapy. A safe and effective drug was also desired to be found for the cancer patients who had bone marrow inhibition and depressed hematopoietic function after chemotherapy. The fusion protein obtained in example 1 was used in this example. The amino acid sequence of the fusion protein is shown in SEQ ID NO: 2.

The BALB/c mice of clean grade (male, 18-20 g) were randomly divided into 5 groups (10 mice in each group) as following:

CTX group: Cyclophosphamide (CTX) was administrated as the dose of 100 mg/kg weight/day for 3 consecutive days with the injection volume of 100 μL. From the 4th day, 100 μL phosphate buffer solution (PBS) was injected every day in the following continuous 6 days.

50 μg group: After cyclophosphamide treatment (100 mg/kg weight/day in 100 μL injection volume) for 3 consecutive days, the fusion protein was injected as the dose of 50 μg/mice/day with the injection volume of 100 μL for the following 6 days;

25 μg group: After cyclophosphamide treatment (100 mg/kg weight/day in 100 μL injection volume) for 3 consecutive days, the fusion protein was injected as the dose of 25 μg/mice/day with the injection volume of 100 μL for the following 6 days;

10 μg group: After cyclophosphamide treatment (100 mg/kg weight/day in 100 μL injection volume) for 3 consecutive days, the fusion protein was injected as the dose of 10 μg/mice/day with the injection volume of 100 μL for the following 6 days;

Normal group: 100 μL phosphate buffer solution (PBS) was injected every day for 9 consecutive days.

Determination indicators were as follows:

(1) The number of peripheral white blood cells (WBC) on 1st day (without cyclophosphamide treatment) and in 2nd-10th day was separately and continuously detected in each group. Briefly, 50 μL peripheral blood was obtained by right-orbital puncture each time and conserved in a tube containing antigoagulant, then the number of white blood cells in peripheral blood was determined in the mode of whole blood with blood cell analyzer.

(2) Bone marrow nucleated cells (BMNC) of each group was determined on the 10th days. Briefly, mice were executed in a sterile environment, soaked in 75% of alcohol for 5 min. The leg muscle of the mice was peeled away and the femur was taken out. The two ends of the femur were clipped by the scissor. From on end, the femur was washed with PBS contained in 5 mL injector. The washing fluid was filtered through a 400 mesh sterile gauze. The filtrate was diluted and adjusted to an appropriate cell concentration. Then the white blood cells were counted with hemocytometer under microscope.

(3) The changes of granulocyte cells in sternal and femoral bone marrow of mice in each group were detected on the 10th days. Briefly, Mice were sacrificed. The femur and sternum was routinely collected, and soaked in 10% formaldehyde solution for 48 h. Then the femur and sternum was fabricated as paraffin section with HE stain. The changes of granulocyte cells were observed under microscope.

(4) The changes of spleen coefficient values in each group were investigated on the 10th day. Briefly, Mice were weighted before execution. Then, the spleen was collected and weighted. The ratio of spleen weight and body weight is the spleen coefficient.

(5) The changes of the ratio of $CD34^+$ of bone marrow mononuclear cells in each group were detected on the 10th day. Briefly, the bone marrow cells were collected according to the method in measurement indicator (2). The cell concentration was adjusted to $5 \times 10^6$ cells/mL. The bone marrow cells were washed with antibody diluent, and the supernatant was abandoned. CD34 (10 μL) antibody was added and cells were incubated for 30 minutes at 4° C. Antibody diluent was added to remove the needless antibody. The supernatant was abandoned after centrifugation. Finally, the antibody preservation solution was added to adjust cell concentration to $1 \times 10^6$ cells/mL. The cells were analyzed with flow cytometry.

(6) The changes of the ratio of $CD45^+$ of bone marrow mononuclear cells in each group were detected on the 10th day. Briefly, the bone marrow cells were collected according to the method in measurement indicator (2). The cell concentration was adjusted to $5 \times 10^6$ cells/mL.

The bone marrow cells were washed with antibody diluent and the supernatant was abandoned after centrifugation. CD45 antibody (10 μL) was added and the cells were incubated for 30 minutes at 4° C. Antibody diluent was added to remove the needless antibody. The supernatant was abandoned after the centrifugation. Finally, the antibody preservation solution was added to adjust cell concentration to $1 \times 10^6$ cells/mL. The cells were analyzed with flow cytometry.

(7) The changes of the colony number of CFU-GM were detected on the 11th day. Briefly, Mice were executed in a sterile environment and soaked in 75% alcohol for 5 min. The leg muscle of the mice was peeled away and the femur was taken out. The two ends of the femur were clipped by the scissor. From on end, the femur was washed with PBS contained in 5 mL injector. The washing fluid was filtered through a 400 mesh sterile gauze. The filtrat was diluted and adjusted to $1 \times 10^5$ cells/mL. 1 mL of washing fluid was centrifuged under a sterile environment and DMEM culture medium (100 μL) was added. Then, gently vortex was made to make the cell suspension completely uniform. 1 mL of methyl cellulose medium was added, and then mixed with 10 μL cell suspension in a freezing tube. Gently vortex was made to make the cell suspension completely uniform. 500 μL of uniform methyl cellulose containing cells was added into each well of the 24-well cell culture plate. The cells are cultured at 37° C. in humidified atmosphere of 5% $CO_2$/95% air for 2 weeks. CFU-GM colonies (more than 50 cells as a colony) were counted under a microscope.

2.2 The purpose of this example was to evaluate the preventive and therapeutical effect of fusion protein for the damage caused by chemotherapy, wherein the fusion protein obtained in example 1 was used.

The mice were randomly divided into three groups, as following:

CTX group: PBS was given every day for 6 consecutive days with the injection volume of 100 μL. From the 7th day, 100 μL cyclophosphamide (100 mg/kg weight/day) was injected every day in the following consecutive 3 days.

Combination group: After fusion protein treatment (50 μg/mice/day in 100 μL injection volume) for 6 consecutive days with the injection volume of 100 μL. From the 7th day, 100 μL cyclophosphamide (100 mg/kg weight/day) was injected every day in the following consecutive 3 days.

Control group: 100 μL phosphate buffer solution (PBS) was injected every day for 9 consecutive days.

All the mice were executed on the 10th day.

Measurement indicators were as follows:

The number of peripheral white blood cells (WBC) was separately detected on 1st day, 8th and 10th day in each group according to the method in example 2.1.

2.3 The purpose of this example was to study the effect of fusion protein on promoting the recovery of the damage of white blood cells caused by chemotherapy, wherein the fusion protein obtained in example 1 was used. The mice were randomly divided into three groups, as following:

CTX group: cyclophosphamide was given for 3 consecutive days as the dose of 100 mg/kg weight/day with the injection volume of 100 μL. From the 4th day, 100 μL PBS was injected every day in the following consecutive 3 days.

Combination group: Fusion protein (50 μg/mice/day in 100 μL injection volume) and cyclophosphamide (100 mg/kg weight/day in 100 μL injection volume) were simultaneously given for 3 consecutive days from the 1st day.

From the 4th day, the fusion protein (50 μg/mice/day in 100 μL injection volume) was injected every day for another consecutive 3 days.

Control group: 100 μL phosphate buffer solution (PBS) was injected every day for 6 consecutive days.

All the mice were executed on the 7th day.

Measurement indicators were as follows:

The number of peripheral white blood cells (WBC) in each group was detected on 1st day, 4th and 7th day according to the method in example 2.1.

Statistical Processing

Each data was expressed in x±s. A t test or an analysis of variance was used after all experimental data were tested for equal variances.

Results:

Table 1 showed the changes of granulocytes of bone marrow cells in sternum of the mice on the 10th day in example 2.1.

TABLE 1

| Group | Granulocyte (%) |
|---|---|
| normal group | 44.3 ± 3.55 |
| CTX group | 22.7 ± 2.18 |
| 50 μg group | 42.6 ± 4.13 |
| 25 μg group | 38.3 ± 3.26 |
| 10 μg group | 35.2 ± 2.28 |

Table 2 showed the changes of granulocytes of bone marrow cells in femur of the mice on the 10th day in example 2.1.

TABLE 2

| Group | Granulocyte (%) |
|---|---|
| normal group | 46.9 ± 4.13 |
| CTX group | 26.5 ± 3.27 |
| 50 μg group | 43.5 ± 3.88 |
| 25 μg group | 37.5 ± 2.98 |
| 10 μg group | 34.5 ± 3.56 |

The results of Table 1 and Table 2 showed the decline of mature granulocytes after the intraperitoneal injection of CTX, characteristic of which is the mild suppression of bone marrow, especially the obviously suppression of granulocytic cells. Nevertheless, the number of granulocytic cells showed the trend of raise after the injection of fusion protein. In the sternum, the number of granulocytic cells in 50 μg group is about 1.8 times that of CTX group. In the femur, the number of granulocytic cells in 50 μg group is about 1.6 times that of CTX group. All above indicated that the fusion protein can restore the proliferation of granulocytes, especially in high dosage group, the number of granulocytes shows no significant difference to normal control group.

FIG. 1 showed that the number of peripherial white blood cells in experimental group has significantly decline compared with that of control group before the injection of fusion protein. The fusion protein is injected from the 4th day via intraperitoneal injection, the number of peripherial white blood cells in all fusion protein treatment groups increases faster than that of single CTX treatment group. On the 10th day, the number of peripherial white blood cells in all fusion protein treatment groups had increased to the normal value or above. In the contrast, the number of peripherial white blood cells of single CTX treatment group was still below to that of the normal control group. The restoration of the white blood cells in peripheral blood showed dose dependent with injection of the fusion protein. Thus it can be seen that the fusion protein can recover the symptoms of leucopenia in the peripheral blood caused by chemotherapy and shorten the recovery time, showing the effect of promoting hematopoiesis.

Figure 2:
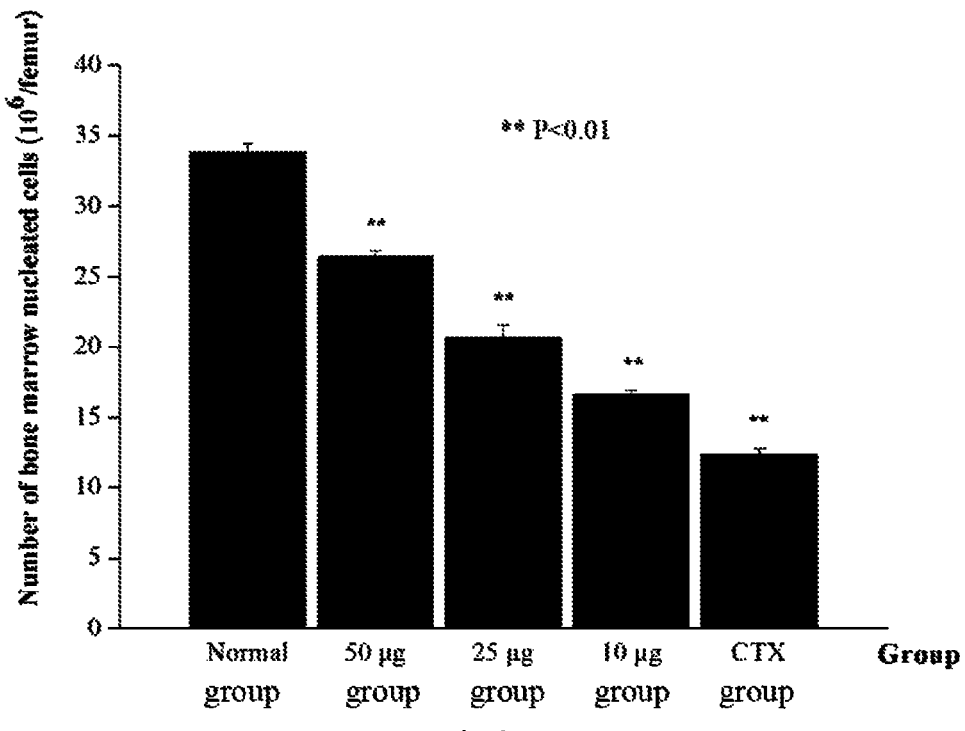
FIG. 2 shows the number of bone marrow nucleated cells (BMNC) of each group on the $10^{th}$ day after chemotherapy.

FIG. 2 showed that after cyclophosphamide was given for 3 consecutive days and then the fusion protein was administrated by intraperitoneal injection in the following 6 days, the number of the bone marrow nucleated cells in 50 μg group is about 2 times that of CTX group (P<0.01). For the rest of the injected dose group, the increasing of the bone marrow nucleated cells was also significantly higher than that of pure CTX group (P<0.01). The effects of different dose groups also have differences in a dose dependent manner. Combined with table 2, the fusion protein can mainly increase neutrophils of the bone marrow cells, indicating that the fusion protein might be used for treating blood disease caused by bone marrow inhibition.

Figure 3:
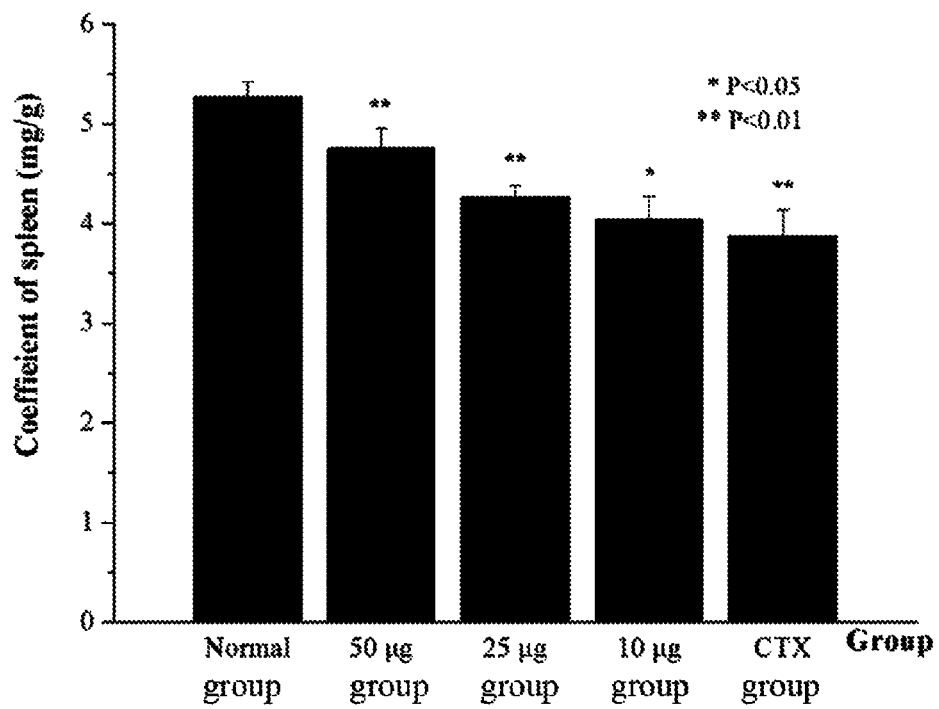
FIG. 3 shows the coefficient of spleen of each group on the $10^{th}$ day after chemotherapy.

FIG. 3 showed that after cyclophosphamide was given for 3 consecutive days and then the fusion protein was administrated by intraperitoneal injection in the following 6 days, in the 10 μg, 25 μg, and 50 μg group, the spleen coefficient was higher than that of pure CTX group, and the spleen coefficient increased with the elevating of the fusion protein concentration (P<0.05~0.01), indicating the obvious dose effect relationship. It demonstrated that the fusion protein can protect the residual hematopoietic stem cells, and promote the extramedullary hematopoiesis.

Figure 4:
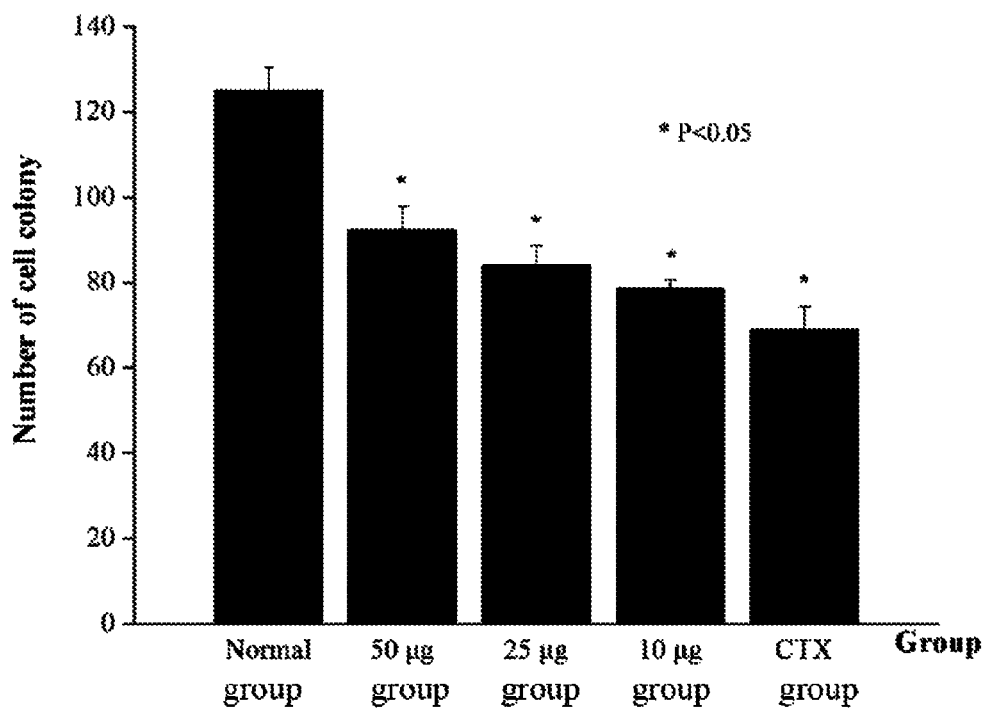
FIG. 4 shows the number of cell colony of each group on the $10^{th}$ day after chemotherapy.

FIG. 4 showed that after cyclophosphamide was given for 3 consecutive days and then the fusion protein was administrated by intraperitoneal injection in the following 6 days, the number of CD34 positive cells in 50 μg group is about 2.8 times of CTX group (P<0.01), and the number of CD34 positive cells in the Mug group is about 2 times of CTX group (P<0.01). Moreover, CD34 positive cells are increased with the elevating of fusion protein concentration (P<0.05), showing the obvious dose effect relationship. Higher number of CD34 cells indicates that hematopoietic system is at the recovery stage, and the fusion protein may stimulate the differentiation of bone marrow mesenchymal stem cells to hematopoietic stem/progenitor cells, improve the hematopoietic microenvironment, and thus promote the recovery of hematopoietic.

Figure 5:
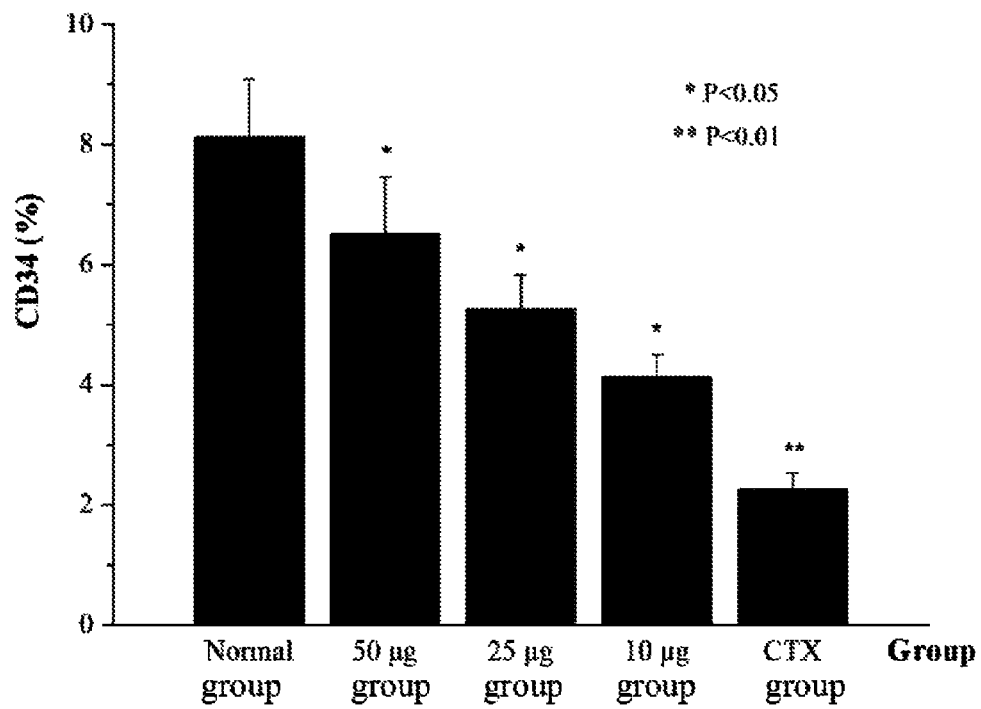
FIG. 5 shows the ratio of CD34 in bone marrow nucleated cells in each group on the $10^{th}$ day after chemotherapy.

FIG. 5 showed that after cyclophosphamide was given for 3 consecutive days and then the fusion protein was administrated by intraperitoneal injection in the following 6 days, the number of CD34 positive cells in 50 μg group is about 1.8 times of CTX group (P<0.001), and the number of CD34 positive cells in the 10 μg group is about 1.5 times of CTX group (P<0.001). Moreover, CD34 positive cells are increased with the increasing of fusion protein concentration (P<0.001), showing the obvious dose effect relationship. Those are in conformity with the changes of the white blood cells in peripheral blood. The changes of the CD34 positive cells further demonstrate that the fusion protein may stimulate the differentiation of bone marrow mesenchymal stem cells to hematopoietic stem/progenitor cells, improve the hematopoietic microenvironment, and thus promote the recovery of hematopoietic.

Figure 6:
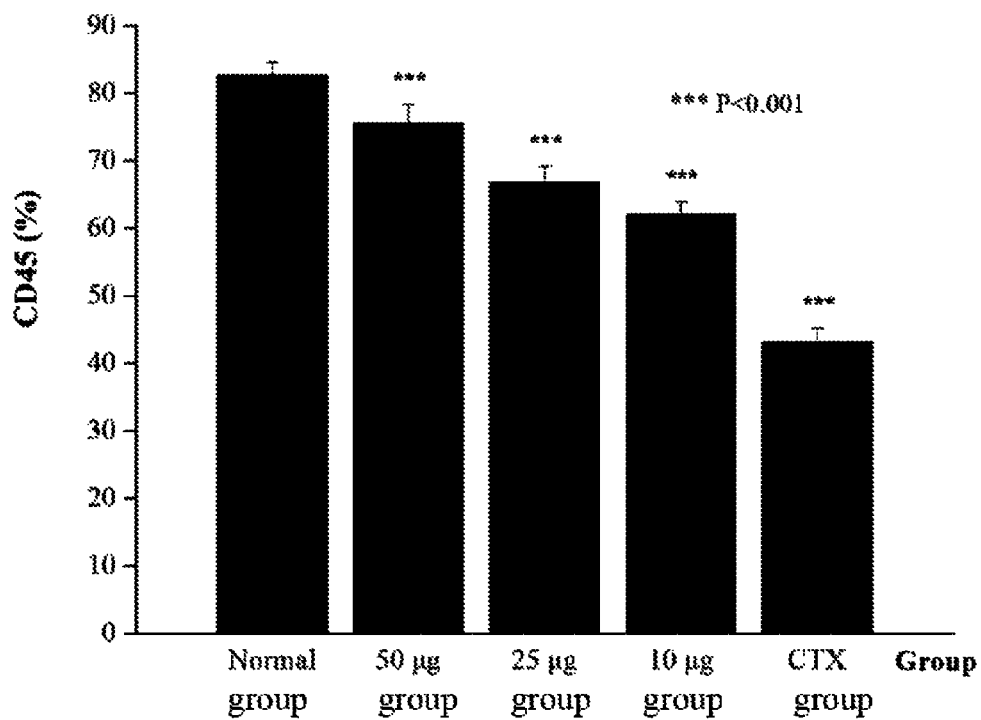
FIG. 6 shows the ratio of CD45 in bone marrow nucleated cells in each group on the $10^{th}$ day after chemotherapy.

FIG. 6 showed that after cyclophosphamide was given for 3 consecutive days and then the fusion protein was administrated by intraperitoneal injection in the following 6 days, the number of granulocyte progenitor cell colony in 50 μg group is about 1.5 times that of CTX group(P<0.05). In the rest of the injected dose group, the increases of the granulocyte progenitor cell colony were also higher than that of pure CTX group. And the colony increased with the elevating of the fusion protein concentration (P<0.05), showing the obvious dose effect relationship. Those results show that the fusion protein may stimulate bone marrow mesenchymal stem cells, improve the hematopoietic microenvironment, and other mechanisms to promote hematopoietic activity.

Table 3 showed the changes of the peripheral white blood cells (WBC) of each group at different time in example 2.2.

TABLE 3

| group | WBC ($10^9$/L) | | |
|---|---|---|---|
| | 1 day | 8 day | 10 day |
| normal group | 8.31 ± 0.23 | 8.62 ± 0.31 | 8.53 ± 0.56 |
| CTX group | 8.28 ± 0.52 | 2.13 ± 0.27 | 1.21 ± 0.19 |
| combination group | 8.19 ± 0.43 | 7.12 ± 0.36 | 5.32 ± 0.25 |

Table 3 showed that the injection of a certain amount of the fusion protein in advance can effectively reduce the descend of the peripheral white blood cells caused by chemotherapy. On the 10th day, the number of the peripheral blood leukocyte of the combination group is about 4.3 times that of CTX group, indicating through injecting the fusion protein in advance, leukopenia caused by chemotherapy can be prevented.

Table 4 showed the leukocyte trends of mice in the peripheral blood in each group in example 2.3.

TABLE 4

| group | WBC ($10^9$/L) | | |
|---|---|---|---|
| | 1 day | 4 day | 7 day |
| normal group | 8.36 ± 0.61 | 8.12 ± 0.58 | 8.25 ± 0.73 |
| CTX group | 7.98 ± 0.38 | 0.97 ± 0.17 | 2.52 ± 0.21 |
| combination group | 8.19 ± 0.53 | 2.82 ± 0.29 | 6.83 ± 0.32 |

Table 4 showed that the fusion protein in combination with CTX can reduce the damage of the peripheral blood leukocytes caused by CTX. On the 4th day, the number of the peripheral blood leukocyte in combination group was about 3 times that of CTX group. After stop using CTX, the recovery of the peripheral blood leukocyte in combination group was faster than that of CTX group, which indicated that fusion protein can be used to repair the reduction of the white blood cells caused by chemotherapy. The above results indicated that, the fusion protein was given simultaneously in the process of chemotherapy, leukopenia caused by chemotherapy or after chemotherapy can be prevented.

Example 3

The Promoting Hematopoiesis of Fusion Protein in the Model of Radiotherapy

The purpose of this example was to observe the therapeutical effect of fusion protein for hematopoietic damage caused by radiotherapy to seek a safe and effective drug for the cancer patients having marrow damage and declined hematopoietic function after radiotherapy. Wherein, the fusion protein fabricated in example 1 was used in this example.

Method:

The BALB/c mice of clean grade (male, 18-20 g) were randomly divided into 3 groups (30 mice in each group), as following:

Radiotherapy group: the mice were irradiated with a single dose of 6.0 Gy. Then, 100 μL phosphate buffer solution (PBS) was injected every day in the following consecutive 2 weeks.

Fusion protein treatment group: After the mice were irradiated with a single dose of 6.0 Gy, the fusion protein was injected as the dose of 50 μg/mice/day with the injection volume of 100 μL in the following consecutive 2 weeks.

Normal group: 100 μL phosphate buffer solution (PBS) was injected every day for consecutive 2 weeks without any other processing.

The number of peripherial white blood cells in all group were detected after dosing. Then, all mice were executed. The number of bone marrow nucleated cells (BMNC) and spleen coefficient of mice were detected according to the method mentioned in example 2. The survival rate of mice was also calculated.

Statistical Processing

Each data was expressed in x±s. A t test or an analysis of variance was used after all experimental data were tested for equal variances.

Results:

The peripheral blood leukocyte of the radiotherapy group decreased significantly compared with the normal group. The peripheral blood leukocytes of the fusion protein group which was injected with fusion protein for two weeks has recovered to normal or above. Thus the fusion protein can restore the reduction of the peripheral blood leucocyte caused by the radiation damage, shorten the recovery period, and show promotion effect of the hematopoiesis.

Table 5 showed the changes of the granulocyte, the bone marrow nucleated cell, the spleen coefficient and the survival rate of mice after the radiotherapy of 2 weeks in each group.

TABLE 5

| group | granulocyte (%) | number of bone marrow nucleated cells ($10^6$ cells/femur) | spleen coefficient (mg/g) | survival rate |
|---|---|---|---|---|
| normal group | 42.1 ± 2.56 | 35.3 ± 1.1031 | 5.69 ± 0.23 | 96.7% |
| radiotherapy group | 11.8 ± 2.13 | 7.6 ± 0.1065 | 1.12 ± 0.11 | 43.3% |
| fusion protein treatment group | 20.3 ± 3.12 | 15.3 ± 0.9863 | 3.32 ± 0.18 | 73.3% |

Table 5 showed that the number of bone marrow granulocyte, the number of bone marrow nucleated cells, the spleen coefficient and the survival rate of the radiation mice which were injected with fusion protein for two weeks were significantly higher than those of the radiotherapy group, wherein the number of bone marrow granulocyte, the number of bone marrow nucleated cells and the spleen coefficient were about two times than those of the radiotherapy group, and the survival rate was by about 1.7 times. It is expected that the fusion protein might be used to treat the disease caused by bone marrow inhibition after radiotherapy.

Example 4

Follow the procedures similar to example 1, except that DAN sequence as shown in SEQ ID NO: 3 was synthetized and the amino acid sequence of the generated fusion protein is shown in SEQ ID NO: 4.

Example 5

Follow the same procedures and grouping method as example 2. The purpose of this example was to evaluate the preventive and/or therapeutical effect of fusion protein fabricated in example 4 for leukopenia caused by chemotherapy, the suppression of bone marrow and the declined hematopoietic function, etc.

The results showed that the raise trend of granulocytic cell numbers after the injection of fusion protein fabricated in example 4. The number of granulocytic cells in sternum in 50 μg group was about 1.9 times that of CTX group. In the femur, the number of granulocytic cells in 50 μg group was about 1.7 times that of CTX group. All above indicated that the fusion protein can restore the proliferation of granulocytes, especially in high dosage group, the number of granulocytes showed no significant difference to normal control group.

After intraperitoneal injection with the fusion protein from the 4th day, the number of peripherial white blood cells in all fusion protein treatment groups increased faster than that of single CTX treatment group. On the 10th day, the number of peripherial white blood cells in all fusion protein treatment groups had increased to the normal value or above. In the contrast, the number of peripherial white blood cells of single CTX group was still below that of the normal control. Thus it can be seen that the fusion protein can recover the peripheral blood leukopenia caused by chemotherapy and shorten the recovery time, showing the effect of promoting hematopoiesis.

After cyclophosphamide was given for 3 consecutive days and then the fusion protein was administrated by intraperitoneal injection for 6 days, the number of the bone marrow nucleated cells in 50 μg group was about 2.2 times that of CTX group ($P<0.01$). In the rest of the injected dose group, the increases of the bone marrow nucleated cells were also significantly higher than that of pure CTX group ($P<0.01$). The effect of varies dose groups also have differences, showing a dose dependent manner. The fusion protein can mainly increase neutrophils of the bone marrow cells. It is indicated that the fusion protein might be used for treating blood disease caused by bone marrow inhibition.

After cyclophosphamide treatment for 3 consecutive days and then intraperitoneal injection of the fusion protein for 6 days, the spleen coefficients in the 10 μg, 25 μg and 50 μg group were higher than that of pure CTX group, and the spleen coefficient increased with the elevating of the fusion protein concentration ($P<0.05\sim0.01$), showing the obvious dose effect relationship. It is indicated that the fusion protein can protect the residual hematopoietic stem cells, and promote the extramedullary hematopoiesis.

After cyclophosphamide treatment for 3 consecutive days and then intraperitoneal injection of the fusion protein for 6 days, the number of CD34 positive cells in 50 μg group was about 2.9 times that of CTX group ($P<0.01$), the number of CD34 positive cells in Mug group was about 2.1 times that of CTX group ($P<0.01$), and the number of CD34 positive cells were increased with elevating of fusion protein concentration ($P<0.05$), showing the obvious dose effect relationship. High number of CD34 cells shows that hematopoietic system is at recovery stage, and the fusion protein may stimulate the differentiation of bone marrow mesenchymal stem cells to hematopoietic stem/progenitor cells, improve the hematopoietic microenvironment, and thus promote the recovery of hematopoietic.

After cyclophosphamide treatment for 3 consecutive days and then the fusion protein was administrated by intraperitoneal injection for 6 days, the number of CD34 positive cells in 50 μg group was about 1.9 times that of CTX group ($P<0.001$), the number of CD34 positive cells in 10 ng group is about 1.6 times that of CTX group ($P<0.001$), and CD45 positive cells were increased with the elevating of fusion protein concentration ($P<0.001$), showing the obvious dose effect relationship. Those are in conformity with the changes of the white blood cells in peripheral blood. The changes of the CD45 positive cells further showed that the fusion protein may stimulate the differentiation of bone marrow mesenchymal stem cells to hematopoietic stem/progenitor cells, improve the hematopoietic microenvironment, and thus promote the recovery of hematopoietic.

As shown in FIG. 6, after cyclophosphamide treatment for 3 consecutive days and then intraperitoneal injection of the fusion protein for 6 days, the number of granulocyte progenitor cell colony in 50 μg group was about 1.7 times that of CTX group ($P<0.05$). In the rest of the injected dose group, the increases of the granulocyte progenitor cell colony were also higher than that of pure CTX group. And the colony increased with the increasing of the concentration of the fusion protein ($P<0.05$), showing the obvious dose effect relationship. Those showed that the fusion protein may promote hematopoietic activity by stimulating bone marrow mesenchymal stem cells, improving the hematopoietic microenvironment, and other mechanisms.

In addition, injection a certain amount of the fusion protein in advance can effectively reduce the decline of the peripheral white blood cells caused by chemotherapy. On the 10th day, the number of the peripheral blood leukocyte of the combination group was about 4.5 times that of CTX group, showing that leukopenia caused by chemothera can be prevented through injecting the fusion protein in advance.

The fusion protein in combination with CTX can reduce the damage of the peripheral blood leukocytes caused by CTX. On the 4th day, the number of the peripheral blood leukocyte in combination group was about 3.5 times that of CTX group. After stop using CTX, the recovery of the peripheral blood leukocyte in combination group was faster than that of CTX group, which indicated that fusion protein can be used to repair the reduction of the white blood cells caused by chemotherapy. From above results, given the fusion protein in the process of chemotherapy can prevent leukopenia caused by chemotherapy or after chemotherapy.

Example 6

Follow the same procedures and grouping method as example 3. The purpose of this example was to evaluate the preventive and/or therapeutical effect of fusion protein fabricated in example 4 for thehematopoietic damage caused by radiootherapy.

The results showed that the peripheral blood leukocyte of the radiotherapy group decreased significantly compared with the normal group. The peripheral blood leukocytes of the fusion protein group which was injected with fusion protein for two weeks have returned to normal or above. The number of bone marrow granulocyte, the number of nucleated cells, spleen coefficient and survival rate of the fusion protein group were significantly higher than those of the radiotherapy group, wherein the number of the bone marrow granulocyte, the number of nucleated cells and spleen coefficient were about two times than those of the radiotherapy group, the survival rate was by about 2 times. Thus the fusion protein can restore the reduction of the peripheral blood leucocyte caused by the radiation damage, shorten the recovery period, and display promoting the hematopoiesis.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method for treating leucopenia which comprises administrating a fusion protein or pharmaceutical composition comprising the same to a subject in need thereof, wherein the fusion protein has the sequence as shown in SEQ. ID NO: 2 or SEQ. ID NO: 4.

2. The method of claim 1, wherein the leucopenia is caused by chemotherapy or radiotherapy.

3. The method of claim 1, wherein the leucopenia is caused by cyclophosphamide.

4. The method of claim 1, wherein the fusion protein or pharmaceutical composition comprising the same is administrated before, during, and/or after radiotherapy or chemotherapy.

5. The method of claim 1, wherein the subject is a mammal.

6. The method of claim 1, wherein the subject is mouse.

7. The method of claim 1, wherein the pharmaceutical composition further comprises cyclophosphamide.

8. The method of claim 1, wherein the pharmaceutical composition further comprises a pharmaceutically acceptable carrier or excipient.

9. The method of claim 1, wherein the fusion protein or pharmaceutical composition comprising the same is administrated by intravenous injection, intraperitoneal injection, or muscle injection.

10. A method for stimulating the differentiation of the bone marrow mesenchymal stem cells to hematopoietic stem/progenitor cells, which comprises administrating a fusion protein or pharmaceutical composition comprising the same to a subject in need thereof, wherein the fusion protein has the sequence as shown in SEQ ID NO:2 or SEQ ID NO: 4, wherein the fusion protein or pharmaceutical composition comprising the same is administrated before, during, and/or after radiotherapy or chemotherapy.

11. The method of claim 10, wherein the subject is mouse.

12. The method of claim 10, wherein the pharmaceutical composition further comprises a pharmaceutically acceptable carrier or excipient.

* * * * *

SEQUENCE LISTING

<160> NUMBER OF SEQ ID NOS: 4

<210> SEQ ID NO 1
<211> LENGTH: 390
<212> TYPE: DNA
<213> ORGANISM: Artificial sequence
<220> FEATURE:
<223> OTHER INFORMATION: fusion protein encoding sequence
<220> FEATURE:
<221> NAME/KEY: CDS
<222> LOCATION: (1)..(390)

<400> SEQUENCE: 1

```
aaa cgt cat gat ggc aaa ggc cat ccg ctg cat aaa cgc gaa aaa cgc        48
Lys Arg His Asp Gly Lys Gly His Pro Leu His Lys Arg Glu Lys Arg
1               5                   10                  15 caa gcc aaa cac aaa cag cgg aaa cgc ctt aag tcc agc tgt aag aga        96
Gln Ala Lys His Lys Gln Arg Lys Arg Leu Lys Ser Ser Cys Lys Arg
            20                  25                  30 cac cct ttg tac gtg gac ttc agt gac gtg ggg tgg aat gac tgg att       144
His Pro Leu Tyr Val Asp Phe Ser Asp Val Gly Trp Asn Asp Trp Ile
        35                  40                  45 gtg gct ccc ccg ggg tat cac gcc ttt tac tgc cac gga gaa tgc cct       192
Val Ala Pro Pro Gly Tyr His Ala Phe Tyr Cys His Gly Glu Cys Pro
    50                  55                  60 ttt cct ctg gct gat cat ctg aac tcc act aat cat gcc att gtt cag       240
Phe Pro Leu Ala Asp His Leu Asn Ser Thr Asn His Ala Ile Val Gln
65                  70                  75                  80 acg ttg gtc aac tct gtt aac tct aag att cct aag gca tgc tgt gtc       288
Thr Leu Val Asn Ser Val Asn Ser Lys Ile Pro Lys Ala Cys Cys Val
                85                  90                  95 ccg aca gaa ctc agt gct atc tcg atg ctg tac ctt gac gag aat gaa       336
Pro Thr Glu Leu Ser Ala Ile Ser Met Leu Tyr Leu Asp Glu Asn Glu
            100                 105                 110 aag gtt gta tta aag aac tat cag gac atg gtt gtg gag ggt tgt ggg       384
Lys Val Val Leu Lys Asn Tyr Gln Asp Met Val Val Glu Gly Cys Gly
        115                 120                 125 tgt cgt                                                                390
Cys Arg
    130
```

<210> SEQ ID NO 2
<211> LENGTH: 130
<212> TYPE: PRT
<213> ORGANISM: Artificial sequence
<220> FEATURE:
<223> OTHER INFORMATION: fusion protein

<400> SEQUENCE: 2

```
Lys Arg His Asp Gly Lys Gly His Pro Leu His Lys Arg Glu Lys Arg
1               5                   10                  15

Gln Ala Lys His Lys Gln Arg Lys Arg Leu Lys Ser Ser Cys Lys Arg
            20                  25                  30

His Pro Leu Tyr Val Asp Phe Ser Asp Val Gly Trp Asn Asp Trp Ile
        35                  40                  45

Val Ala Pro Pro Gly Tyr His Ala Phe Tyr Cys His Gly Glu Cys Pro
    50                  55                  60

Phe Pro Leu Ala Asp His Leu Asn Ser Thr Asn His Ala Ile Val Gln
65                  70                  75                  80

Thr Leu Val Asn Ser Val Asn Ser Lys Ile Pro Lys Ala Cys Cys Val
                85                  90                  95
```

```
Pro Thr Glu Leu Ser Ala Ile Ser Met Leu Tyr Leu Asp Glu Asn Glu
            100                 105                 110

Lys Val Val Leu Lys Asn Tyr Gln Asp Met Val Val Glu Gly Cys Gly
        115                 120                 125

Cys Arg
    130

<210> SEQ ID NO 3
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 3 caa gcc aaa cac aaa cag cgg aaa cgc ctt aag tcc agc tgt aag aga      48
Gln Ala Lys His Lys Gln Arg Lys Arg Leu Lys Ser Ser Cys Lys Arg
1               5                   10                  15 cac cct ttg tac gtg gac ttc agt gac gtg ggg tgg aat gac tgg att      96
His Pro Leu Tyr Val Asp Phe Ser Asp Val Gly Trp Asn Asp Trp Ile
            20                  25                  30 gtg gct ccc ccg ggg tat cac gcc ttt tac tgc cac gga gaa tgc cct     144
Val Ala Pro Pro Gly Tyr His Ala Phe Tyr Cys His Gly Glu Cys Pro
        35                  40                  45 ttt cct ctg gct gat cat ctg aac tcc act aat cat gcc att gtt cag     192
Phe Pro Leu Ala Asp His Leu Asn Ser Thr Asn His Ala Ile Val Gln
    50                  55                  60 acg ttg gtc aac tct gtt aac tct aag att cct aag gca tgc tgt gtc     240
Thr Leu Val Asn Ser Val Asn Ser Lys Ile Pro Lys Ala Cys Cys Val
65                  70                  75                  80 ccg aca gaa ctc agt gct atc tcg atg ctg tac ctt gac gag aat gaa     288
Pro Thr Glu Leu Ser Ala Ile Ser Met Leu Tyr Leu Asp Glu Asn Glu
                85                  90                  95 aag gtt gta tta aag aac tat cag gac atg gtt gtg gag ggt tgt ggg     336
Lys Val Val Leu Lys Asn Tyr Gln Asp Met Val Val Glu Gly Cys Gly
            100                 105                 110 tgt cgt                                                             342
Cys Arg

<210> SEQ ID NO 4
<211> LENGTH: 114
<212> TYPE: PRT
<213> ORGANISM: Homo sapiens

<400> SEQUENCE: 4

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80
```

```
Pro Thr Glu Leu Ser Ala Ile Ser Met Leu Tyr Leu Asp Glu Asn Glu
                85                  90              95

Lys Val Val Leu Lys Asn Tyr Gln Asp Met Val Val Glu Gly Cys Gly
            100                 105             110

Cys Arg
```